US00PP23383P2

(12) United States Plant Patent
Ferguson et al.

(10) Patent No.: US PP23,383 P2
(45) Date of Patent: Feb. 12, 2013

(54) STRAWBERRY PLANT NAMED 'DRISSTRAWTWENTY'

(50) Latin Name: *Fragaria×ananassa*
Varietal Denomination: DrisStrawTwenty

(75) Inventors: Michael D. Ferguson, Moorpark, CA (US); Jorge Rodriguez Alcazar, Texcoco (MX)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 13/317,146

(22) Filed: Oct. 11, 2011

(51) Int. Cl.
*A01H 5/00* (2006.01)

(52) U.S. Cl. ..... Plt./208

(58) Field of Classification Search ..... Plt./208
See application file for complete search history.

*Primary Examiner* — Annette Para
(74) *Attorney, Agent, or Firm* — Jondle & Associates, P.C.

(57) ABSTRACT

A new and distinct variety of strawberry plant named 'DrisStrawTwenty' characterized by having large, conical fruit with medium sweetness and high yield is disclosed.

3 Drawing Sheets

Genus and species: *Fragaria×ananassa.*
Variety denomination: 'DrisStrawTwenty'.

BACKGROUND OF THE NEW PLANT

The present invention relates to a new and distinct strawberry variety designated 'DrisStrawTwenty' and botanically known as *Fragaria×ananassa*. This new strawberry variety was the result of a controlled cross conducted in Ventura County, Calif., in February 2005 between the proprietary female parent '2K297' (unpatented) and the male parent 'Driscoll Ojai' (U.S. Plant Pat. No. 18,575). A single plant was selected for asexual propagation via tissue culture and vegetative cuttings in Shasta County, Calif. in February 2005.

'DrisStrawTwenty' underwent further testing in Ventura County, Calif. for five years (2006-2011). The present invention has been found to retain its distinctive characteristics through several asexual propagations via stolons.

Plant Breeder's Rights for this variety were applied for in Mexico on Aug. 29, 2011. 'DrisStrawTwenty' has not been made publicly available or sold more than one year prior to the filing date of this application.

SUMMARY OF THE INVENTION

The following are the most outstanding and distinguishing characteristics of this new cultivar when grown under normal horticultural practices in Ventura County, Calif.

1. High yield;
2. Large, conic shaped fruit; and
3. Medium sweetness.

DESCRIPTION OF THE PHOTOGRAPHS

The accompanying color photographs show typical specimens of the new variety at various stages of development. The colors shown are as true as can be reasonably obtained by conventional photographic procedures. The photographs were taken from eight-month-old plants.

DESCRIPTION OF THE NEW VARIETY

Figure 1:
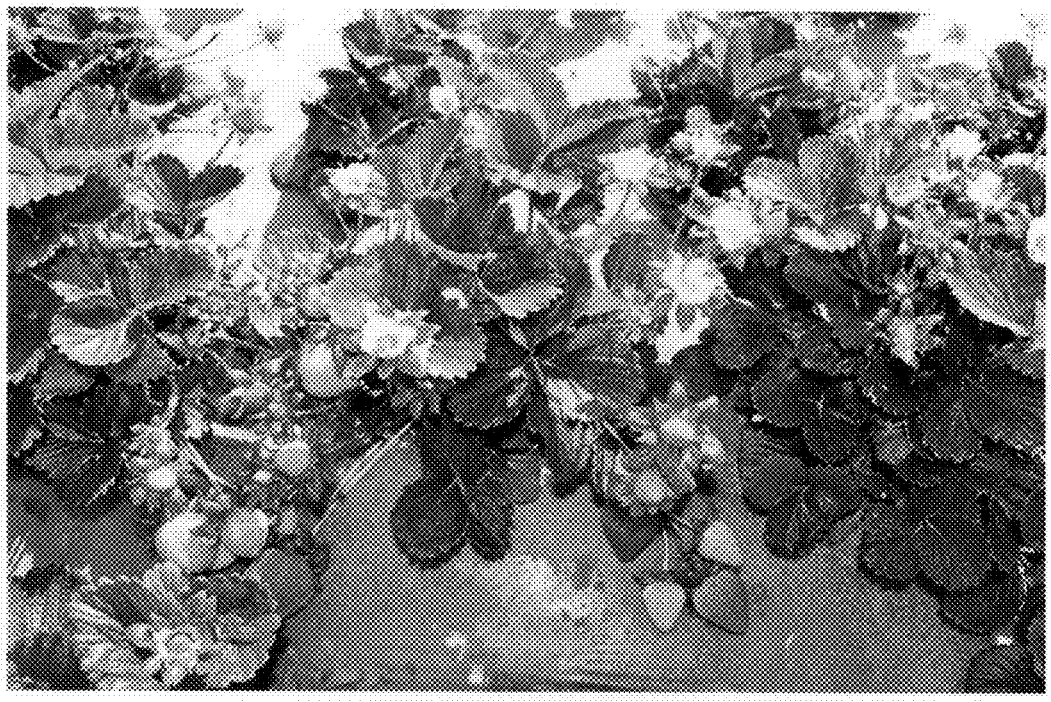
FIG. 1 shows overall plant habit including fruit at various stages of development.
Figure 2:
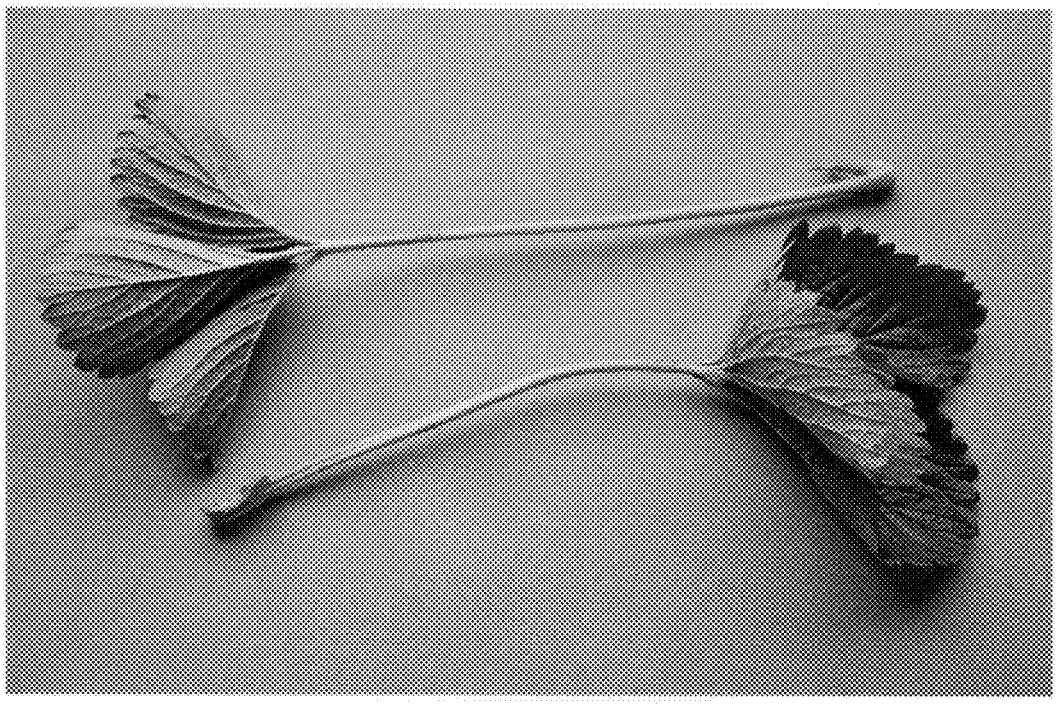
FIG. 2 shows leaves of the plant with three leaflets.
Figure 3:
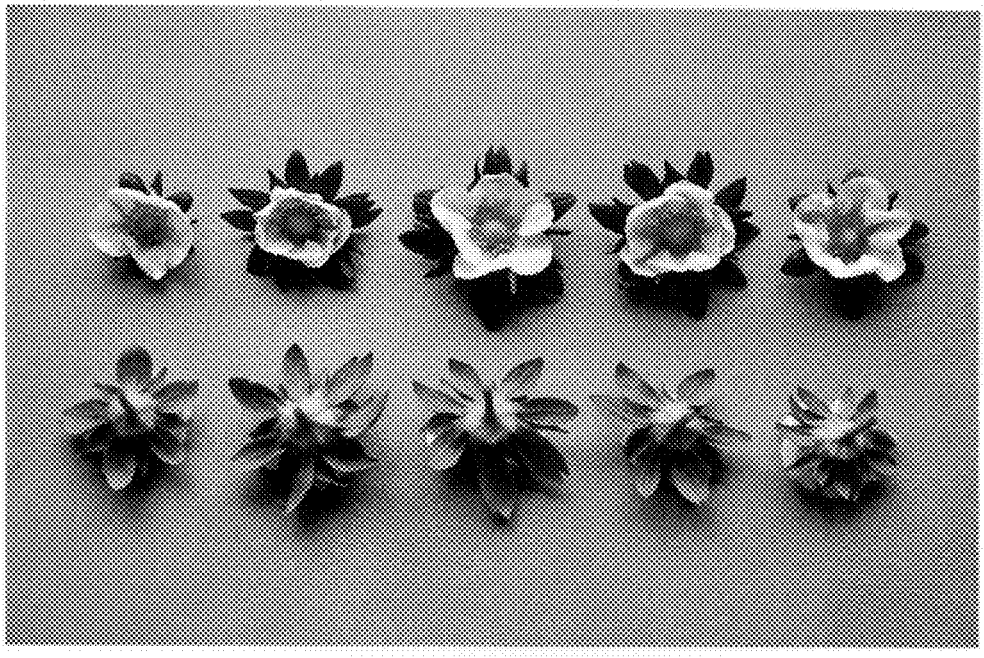
FIG. 3 shows both upper and lower surfaces of the flowers.
Figure 4:
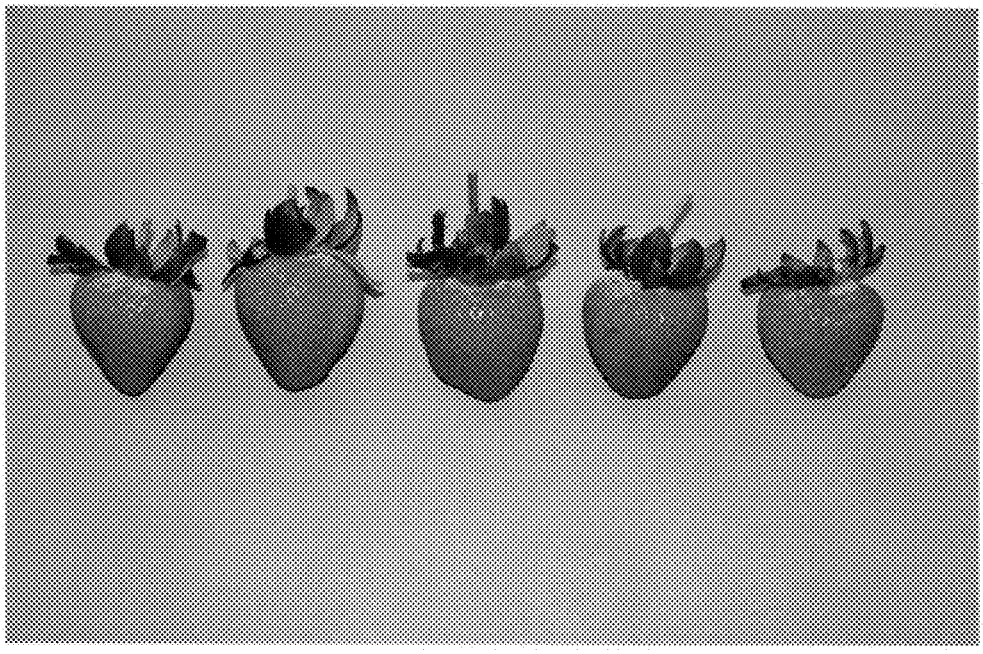
FIG. 4 shows the whole fruit.
Figure 5:
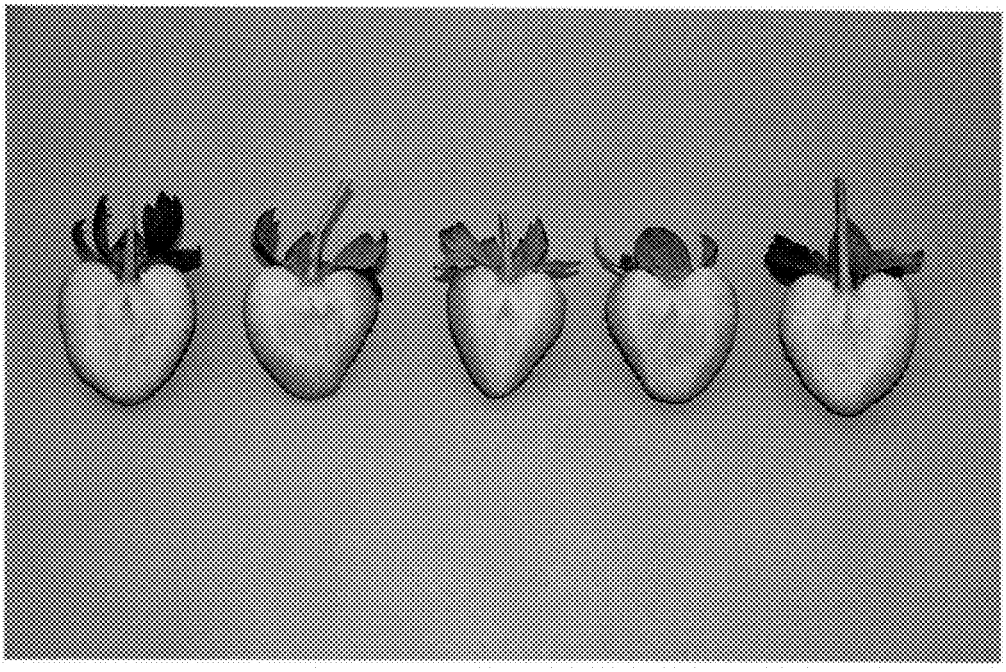
FIG. 5 shows the fruit in longitudinal cross-section.

The following detailed descriptions set forth the distinctive characteristics of 'DrisStrawTwenty'. The data which define these characteristics is based on observations taken in Ventura County, Calif. from 2006 to 2011. This description is in accordance with UPOV terminology. Color designations, color descriptions, and other phenotypical descriptions may deviate from the stated values and descriptions depending upon variation in environmental, seasonal, climatic, and cultural conditions. 'DrisStrawTwenty' has not been observed under all possible environmental conditions. The botanical description of 'DrisStrawTwenty' was taken from eight-month-old plants. Color terminology follows The Royal Horticultural Society Colour Chart, London (R.H.S.) (2001 edition). Descriptive terminology follows the *Plant Identification Terminology, An Illustrated Glossary,* $2^{nd}$ edition by James G. Harris and Melinda Woolf Harris, unless where otherwise defined.

DETAILED BOTANICAL DESCRIPTION OF THE PLANT

Classification:
- *Species.*—*Fragaria×ananassa.*
- *Common name.*—Strawberry.
- *Denomination.*—'DrisStrawTwenty'.

Parentage:
- *Female parent.*—The proprietary variety '2K297' (unpatented).
- *Male parent.*—The variety 'Driscoll Ojai' (U.S. Plant Pat. No. 18,575).

Plant:
- *Height.*—16.9 cm.
- *Diameter.*—28.1 cm.
- *Number of crowns/plant.*—3.
- *Habit.*—Globose — semi-upright.

*Density of individual plant*.—Medium.
*Vigor* (*health and hardiness of plant*).—Strong.
Terminal leaflets:
*Size*.—Medium. Length: 68.0 mm. Width: 60.7 mm. Length/width ratio: 1.1.
*Number of teeth/terminal leaflet*.—18.
*Shape of teeth*.—Rounded-crenate.
*Color*.—Upper surface: Medium; RHS 147A (Medium green). Lower surface: Light; RHS 142B (Light yellow-green).
*Shape in cross section*.—Concave.
*Blistering*.—Medium.
*Glossiness*.—Medium.
*Number of leaflets*.—3 only.
*Shape*.—Orbicular.
*Base shape*.—Acute.
*Apex descriptor*.—Rounded.
*Variegation*.—Absent.
*Margin*.—Serrate.
*Margin profile*.—Involute (margins rolled inwards).
Petiole:
*Length*.—Long; 15.8 cm.
*Diameter*.—3.11 mm.
*Pubescence*.—Medium.
*Pose of hairs*.—Outwards — horizontal.
*Color*.—RHS 143C (Medium green).
Petiolule:
*Length*.—12.16 mm.
*Diameter*.—1.88 mm.
*Bract frequency*.—0 or 2.
*Color*.—RHS 143C (Medium green).
Stipule:
*Length*.—3.5 cm.
*Width*.—17.87 mm.
*Pubescence*.—Absent or very sparse.
*Anthocyanin coloration*.—Absent or very weak.
Stolon:
*Number*.—Many.
*Average number of daughter plants per plant*.—28.
*Anthocyanin coloration*.—Absent or very weak.
*Thickness*.—Medium.
*Pubescence*.—Absent or very sparse.
Inflorescence:
*Position relative to foliage*.—Above.
*Number of flowers*.—Many.
*Time of flowering* (50% *of plants at first flower*).—Late.
*Flower size*.—Medium.
*Flower diameter*.—20.71 mm.
*Petals*.—Shape: Orbicular. Apex: Convex. Base: Concave-convex. Margin: Entire. Spacing: Touching. Length: 8.7 mm. Width: 9.26 mm. Length/width ratio: 0.9; As long as broad. Typical and observed petal number per flower: 6. Color (upper surface): RHS 155C (White).
*Calyx*.—Diameter: 25.82 mm. Diameter relative to corolla: Larger. Inner calyx diameter relative to outer: Same size. Insertion of calyx: Set above fruit — raised. Pose of calyx segments: Reflexed — upwards. Size of calyx in relation to fruit: Slightly larger. Adherence of calyx: Medium.
*Sepal*.—Shape: Elliptical and ovate. Apex: Truncate. Margin: Entire. Length: 9.93 mm. Width: 4.81 mm. Typical and observed sepal number per flower: 10 or 12.
*Receptacle color*.—RHS 145A (Yellow-green).
*Stamen*.—Present. Anther color: RHS 163B (Greyed-orange).
*Pedicel*.—Attitude of hairs: Outwards — horizontal.
Fruiting truss:
*Length*.—Long; 17.5 cm.
*Diameter at base of truss*.—2.67 mm.
*Number of berries per fruiting truss*.—1.
*Attitude at first picking*.—Erect.
*Color at base of truss*.—RHS 246D (Yellow-green).
Fruit:
*Relative fruit size*.—Large.
*Length*.—45.64 mm.
*Width*.—38.45 mm.
*Length/width ratio*.—1.2; as long as broad.
*Fruit hollow length*.—24.69 mm.
*Fruit hollow width*.—10.08 mm.
*Fruit hollow length/width ration*.—2.5.
*Fruit hollow center* (*cavity*).—Medium.
*Weight* (*per individual berry*).—25.8 g.
*Predominant fruit shape*.—Conical.
*Difference in shape between primary and secondary fruits*.—None or very slight.
*Evenness of fruit surface*.—Even or very slightly uneven.
*Fruit skin color*.—RHS 46A (Medium red).
*Evenness of fruit color*.—Even or very slightly uneven.
*Fruit glossiness*.—Strong.
*Achenes*.—Insertion of achenes: Below surface. Coloration (sunward side of berry): RHS N144B (Yellow-green). Coloration (shaded side of berry): RHS 145A (Yellow-green). Number per berry: 461. Weight (weight achenes divided by total # seed): 0.000520607373. Band without achenes: Medium.
*Firmness of flesh*.—Firm.
*Color of flesh* (*excluding core*).—RHS 2B (Light red) and RHS 155B (White).
*Color of core*.—RHS 155B (White) and RHS 44B (Medium-red).
*Evenness of flesh color*.—Slightly uneven.
*Distribution of flesh color*.—Marginal and central.
*Sweetness*.—Medium.
*Acidity*.—Weak.
*Texture when tasted*.—Medium.
*Type of bearing*.—Not everbearing — not remontant.
*Grams of fruit/plant*.—544.
*Harvest interval*.—Late November to early April.
*Harvest maturity*.—Late.
Disease, pest, and stress resistance:
*Powdery mildew*.—Resistant.
*Xanthomonas fragariae*.—Resistant.
*Tetranychus urticae*.—Moderately resistant.

COMPARISON WITH PARENTAL VARIETIES

When 'DrisStrawTwenty' is compared to the proprietary female parent '2K297' (unpatented), 'DrisStrawTwenty' is less vigorous, higher yielding, has a more conic fruit shape and has better flavor than '2K297'.

When 'DrisStrawTwenty' is compared to the male parent 'Driscoll Ojai' (U.S. Plant Pat. No. 18,575), 'DrisStrawTwenty' has a higher yield, larger fruit and a longer production season than 'Driscoll Ojai'.

We claim:

1. A new and distinct variety of strawberry plant as described and shown herein.

* * * * *